United States Patent [19]

Gautier

[11] Patent Number: 5,108,448
[45] Date of Patent: Apr. 28, 1992

[54] CUP INTENDED TO BE FIXED CEMENTLESSLY FOR A TOTAL HIP PROSTHESIS

[75] Inventor: Jean E. Gautier, Lyons, France

[73] Assignee: High Tech Industries S.A., Chassieu, France

[21] Appl. No.: 500,876

[22] Filed: Mar. 29, 1990

[30] Foreign Application Priority Data

Apr. 5, 1989 [FR] France .................. 89 04699

[51] Int. Cl.⁵ ........................... A61F 2/34
[52] U.S. Cl. .................................... 623/22
[58] Field of Search ............. 623/16, 18, 19, 20, 623/22, 23

[56] References Cited

U.S. PATENT DOCUMENTS

| 4,535,486 | 8/1985 | Roberts et al. | 623/22 |
|---|---|---|---|
| 4,687,487 | 8/1987 | Hinterman | 623/22 |
| 4,795,469 | 10/1989 | Oh | 623/22 |
| 4,834,759 | 5/1989 | Spotorno | 623/22 |
| 4,878,918 | 11/1989 | Tari et al. | 623/22 |
| 4,969,910 | 11/1990 | Frey et al. | 623/22 |

FOREIGN PATENT DOCUMENTS

| 0137644 | 4/1985 | European Pat. Off. | 623/22 |
|---|---|---|---|
| 0308297 | 3/1989 | European Pat. Off. | 623/22 |
| 2266491 | 4/1974 | France . | |
| 2416004 | 2/1978 | France . | |
| 2595562 | 3/1986 | France . | |
| 2617040 | 6/1987 | France . | |
| 2639822 | 6/1990 | France | 623/22 |
| 8605679 | 10/1986 | PCT Int'l Appl. | 623/22 |

OTHER PUBLICATIONS

Biomaterials an Introduction by Joon Bu Park-Library of Congress 1979 Plenum Press, New York pp. 215-125.

Primary Examiner—David J. Isabella
Attorney, Agent, or Firm—Oliff & Berridge

[57] ABSTRACT

This cup is of the type composed of three spherical caps (2, 3, 4), namely:
  an outer cap (2) made of a rigid material whose outer face is provided with radial roughnesses (11) designed for it to be attached in the acetabulum,
  an inner cap (3) made of hard, biocompatible material with a low friction coefficient,
  and an intermediate cap (4) made of a semi-rigid material, and in the outer cap (2) of which are cut out radially movable tongues (5) shaped like portions of spherical-cap sectors, defined by arcuate slots (5).

Arcuate slots (5) extend between two circles parallel to the opening plane (2b) of this cap, one of which slots is located near this plane and the other is located near the top (2c) of the cap, the ends of these slots (5) located near top (2c) of cap (2l also being connected, two by two, by partially annular slots (7) coinciding with the aforesaid circle which is located near the top (2c) of cap (2).

12 Claims, 4 Drawing Sheets

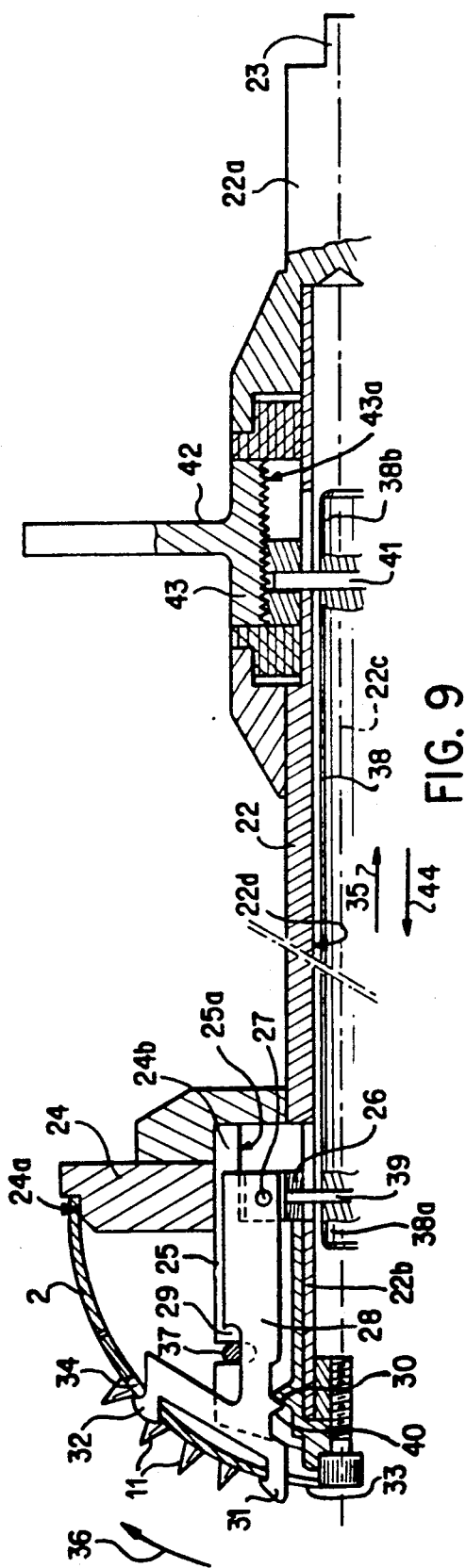
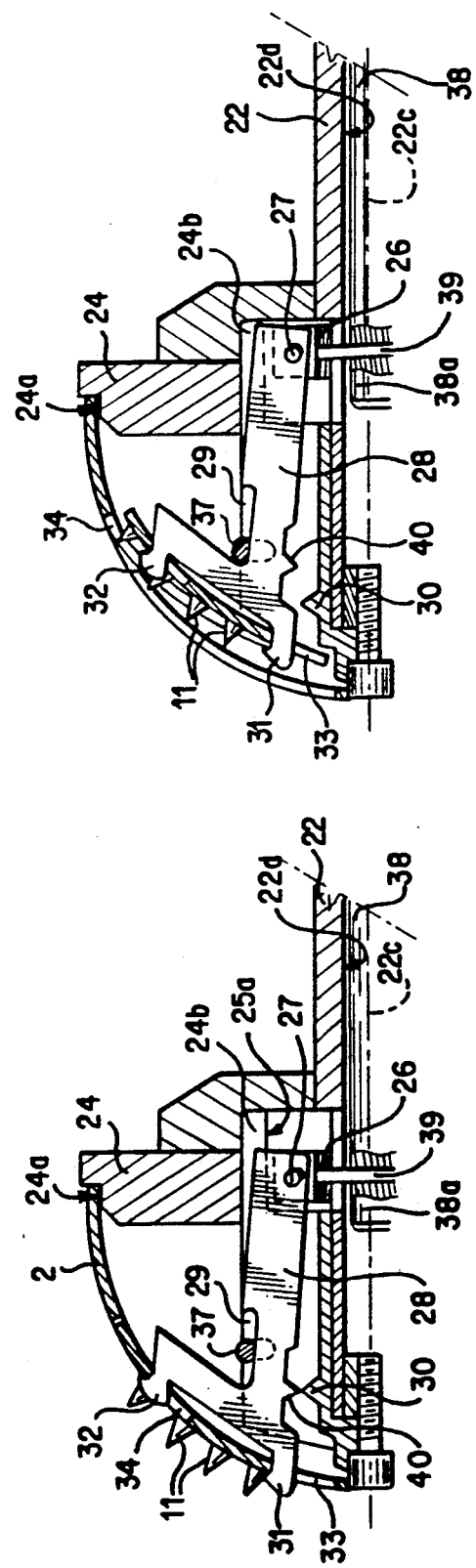
FIG. 9
FIG. 10
FIG. 11

5,108,448

CUP INTENDED TO BE FIXED CEMENTLESSLY FOR A TOTAL HIP PROSTHESIS

BACKGROUND OF THE INVENTION

The present invention relates to a cup intended to be fixed cementlessly for a total hip prosthesis.

Description of the Prior Art

Apart from the fitting difficulties which they present, in particular for screwed cups, cups which are currently fixed cementlessly are often unsatisfactory as they do not have sufficient stability over time.

At first these cups were made from an outer spherical shell made from a rigid biocompatible material, such as stainless steel, carrying on its outer face means for fixing it in the bone of the cotyloid cavity, such as securing spikes, a cylindrical or conical screwthread, or other similar means, an inner spherical shell made from a material, such as high-density polyethylene, having a small coefficient of friction relative to the material forming the cephalic head of the femoral element, which is generally stainless steel or ceramic, being fixed in any suitable manner in the inner cavity of the outer shell.

Now it is likely that the lack of stability over time of these cups essentially originates from the fact that vertical forces, direct or resultant, are transmitted to the cups without being cushioned by an elastic layer.

In an attempt to overcome this disadvantage, cups have been designed having an intermediate spherical shell made from a flexible and elastic material, such as those described in European Patent 0,066,092 and in patent application PCT WO 86/02261 and European Patent Application 0,253,941. In these cups, however, the inner spherical shells proved to be too loose relative to the outer spherical shell fixed in the acetabulum, which resulted in increased risks of dislocation.

European Patent Applications 0,169,978 and 0,242,633 describe a cup having two elements, namely:

an outer spherical shell made from a rigid biocompatible material, such as stainless steel, the outer face of which is provided with substantially radial projections or "spikes" intended to enable it to be fixed into the cotyloid cavity, an inner spherical shell made from semi-rigid, biocompatible and preferably elastic material, such as a plastic such as high-density polyethylene, in which cup the outer shell is made expansible by the presence of tongues in the form of portions of sectors of the spherical shell, separated from each other by slits in arcs of a circle, having a regular angular distribution and capable of being displaced radially outwards when this shell is positioned and fixed in the cotyloid cavity.

The intended objective of this cup was to improve its retention in the acetabulum by causing its outer shell to expand radially after being positioned. In this cup, however, the slits in arcs of a circle which define the radially movable tongues do not extend as far as the vertex of this shell and join the peripheral edge of the opening of its cavity such that the tongues are only retained by their narrow end close to the vertex of the shell and that as a result the diameter of the opening of the cavity of this shell may expand when it is subjected to substantial forces and prolonged repetition of this expansion obviously shakes the cup by degrees, causing its retention in the acetabulum to deteriorate progressively.

Furthermore, the deformation of the opening of this cup has the disadvantage of promoting the loosening of the shell in the cotyloid cavity. Indeed, the diametral splaying under force causes, by reaction, the shell to lift. Additionally, this lack of diametral rigidity increases the risks of dislocation and virtually prevents the use of an intermediate shell made from a sufficiently flexible and elastic material to absorb the impacts and substantial forces sustained by a rigid inner shell.

SUMMARY OF THE INVENTION

The present invention aims to overcome all these disadvantages. To this end, in the cup to which it relates, and which is of the 3-element type, composed of three shells fitted into each other, the outer one of which has tongues which can move radially, in the form of portions of sectors of a spherical shell, defined by slits in arcs of a circle, having a regular angular distribution, the slits in arcs of a circle extend between two circles parallel to the plane of the opening of this shell, one situated near this plane and the other situated near the vertex of the shell, the ends of these slits situated near the vertex of the shell furthermore being connected in pairs by partially annular slits coinciding with that one of the abovementioned circles situated near the vertex of the shell, such that all the abovementioned tongues are retained by their large-sized end situated near the opening of the shell and that the small-sized end of a tongue, in other words every other portion of a sector of a spherical shell, can be displaced radially inwards or outwards, only the tongues, which can move radially, carrying securing spikes, on their outer surface.

The slits in arcs of a circle which establish the tongues of this shell thus do not join the edge of its opening, with the result that the latter may not be expanded, which ensures excellent retention of this cup in the acetabulum by its diametral band.

It should, however, be noted that the movement, which is virtually nil, of retracting the ends of the tongues closest to the opening of the cup is incompatible with the presence of spikes near this end of the tongues.

In order to overcome this, according to an improved embodiment of this cup, which aims to obtain substantially the same degree of anchoring over the entire outer surface of this cup, from each tongue connected to the outer shell by its large-sized end nearest the opening of this shell, in other words in each main tongue, a secondary tongue is cut out which is inverted in relation to the first, in other words is connected to the latter by its end nearest the vertex of this shell, and the free end of which is near the opening of this shell and the outer surface of which is covered with securing spikes up to a point near its free edge.

After the outer shell has been positioned, the presence of the secondary tongues therefore enables it to be caused to expand near its opening, something which the presence of the main tongues alone does not allow, and thus ensures a better fastening for it in the acetabulum.

Furthermore, the presence of the secondary tongues whose outer surface carries securing spikes which are capable of being retracted by the secondary tongues bending towards the inside of the shell, enables this cup to be positioned and withdrawn easily, in spite of the presence of securing spikes carried by the secondary tongues, near the base of the main tongues, in other words near the opening of this outer shell, this presence considerably improving the retention of this cup in the acetabulum.

When this cup is fitted. its outer shell is perfectly spherical and has no projecting point, all the tongues carrying the spikes being in a position withdrawn by an appropriate mechanism. The outer shell is easy to position since it is displaced unhindered in the matching spherical cavity formed in the cotyloid cavity. As a result of this easy displacement, it is a simple matter to adjust the angle of the cup accurately. Once this shell is engaged in the location provided to receive it, in the cotyloid cavity, its movable tongues held inside it are then freed and positioned by engaging an impaction or impacting tool into its cavity before the preassembled intermediate and inner shells are positioned in this cavity.

According to a simple embodiment of the invention, the means for positioning or withdrawing this cup comprise, on the one hand, meridian notches or slots provided in the main and secondary tongues, near their free end, and, on the other hand, a device having, in addition to a tubular neck which can be adapted to the known traditional means for setting and adjusting the angle of orientation of the cup, a head in the form of a circular plate carrying, on its surface opposite that of the neck, on the one hand a cylindrical shoulder for centering the outer shell and having for this purpose the same diameter as the inner edge of its opening and, on the other hand, hook levers whose hinge pins, orthogonal to the axis of the neck, enable them to pivot between a retracted position of the hooks, in other words close to the axis of the neck, and an active catching position in the bottom of a tongue notch or slot, in other words moved away from the axis of the neck, each lever carrying two hooks and the levers and their hooks having the same angular distribution as the notches or slots and each hook itself being arranged so as to be capable of being engaged, in the retracted position, into a notch or slot of a tongue when the lever which carries it is displaced in a direction corresponding to its movement away from the abovementioned plate, means being provided to enable the hinge pins of the levers to be displaced in one or other direction, parallel to the axis of the neck, while other means are provided to pivot the levers into the catching position when, after they have engaged in the notches or slots, their hinge pins are displaced towards the plate, thus causing all the tongues to be bent into the retracted position.

This device may therefore be used both for positioning and withdrawing this outer shell.

According to a preferred embodiment of the invention, the means for displacing the hinge pins of the hook levers in both directions, parallel to the axis of the neck, comprise, in combination, a collar supporting these pins and mounted, so as to be movable axially, in a cylindrical recess of a cylindrical piece coaxial with the plate and having radial notches, each of which serves to house and guide a hook lever, a control rod coaxial with the plate and with the neck, in the bore of which it is housed, one end of which is connected axially by a pin or other similar means to the collar supporting the hinge pins of the hook levers and the other end of which is connected axially to a threaded ring mounted in a tapped bore of an operating wheel carried by the neck, this threaded ring being furthermore connected in rotation to the neck, for example by a pin traversing the threaded ring, the relative end of the control rod and diametrically opposite longitudinal slots of the tubular neck.

In order to displace the hinge pins of the levers parallel to the axis of the neck, it is thus sufficient to pivot the operating wheel in the direction corresponding to the direction of the desired displacement, all the time holding the neck to prevent it from pivoting.

Furthermore, according to a simple embodiment of the invention, the means for pivoting the hook levers from their retracted position to their catching position comprise, on the one hand, a projection carried by each bottom of a radial notch serving for housing and guiding a hook lever and with which an opposite projection is associated, carried by the radially innermost surface of each hook lever, these projections being arranged such that the second mounts the first as soon as, from their position furthest away from the plate, the hinge pins of the levers are displaced towards the plate and, on the other hand, an annular spring means surrounding the hook levers and acting on them in order to constantly tend to return them to the retracted position.

With this device, when the outer shell is correctly positioned in the acetabulum, the operating wheel then need only be rotated in the opposite direction to free all the tongues and to allow them to resume their original position. However, the resistance which their spikes encounter in the acetabulum does not allow them to return to their original position, with the result that, as they begin to return, the surgeon ceases to pivot the operating wheel and applies, for example using a flyweight, a few axially directed shocks to the neck.

According to a preferred feature of the invention, which aims to reduce the time spent fitting this cup, the intermediate shell is fixed to the outer shell by a bayonet fastening system or by snap-fitting a flange into a throat, which enables fixing to be carried out more quickly and more easily than when using a screwthread, and the inner shell is fixed to the intermediate shell by a snap-fit.

It should be noted that the composition of this cup enables close contact to be maintained constantly not only between its three shells but also with the cotyloid cavity, which virtually eliminates a risk of displacement and guarantees an excellent distribution of the loads. Indeed, any pressure applied to the securing tongues causes, by reaction, the shell to press against the base of the cotyloid cavity.

The invention will, in any case, be clearly understood from the description which follows, made with reference to the attached schematic drawings showing by way of non-limiting example an embodiment of this cup:

BRIEF DESCRIPTION OF THE DRAWINGS

FIG. 9 is a view in axial cross-section of the device in FIG. 8 with its tongues in the normal position;

FIGS. 10 and 11 are partial cross-sectional views showing the head of the impaction device in two successive positions of bringing the tongues into the retracted position.

DESCRIPTION OF THE PREFERRED EMBODIMENTS

Figure 2:
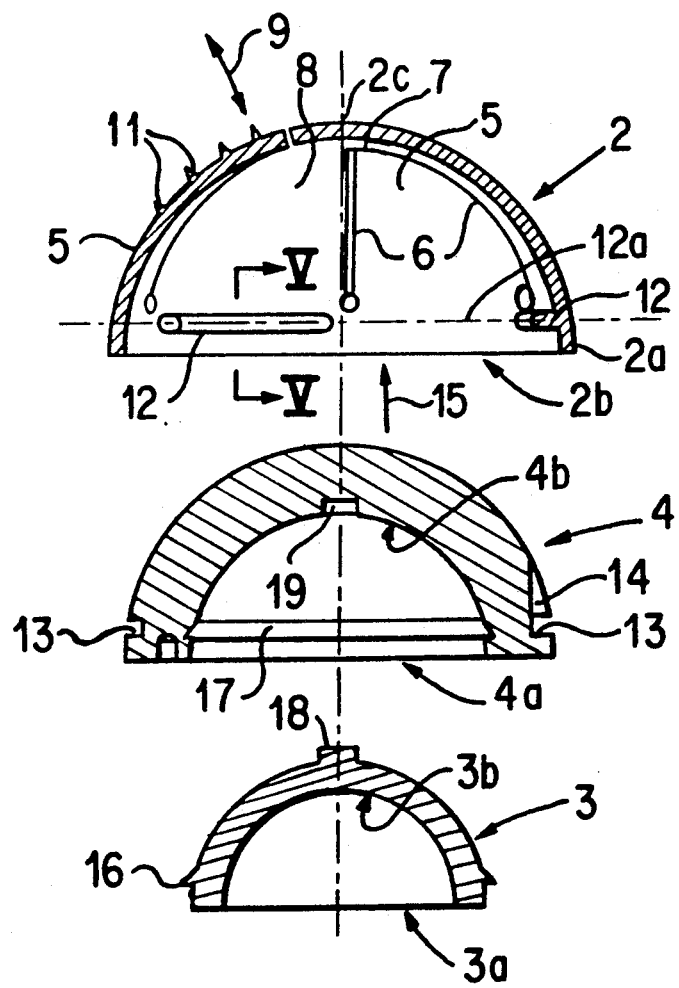
FIG. 2 is an exploded side view in axial cross-section.
Figure 3:
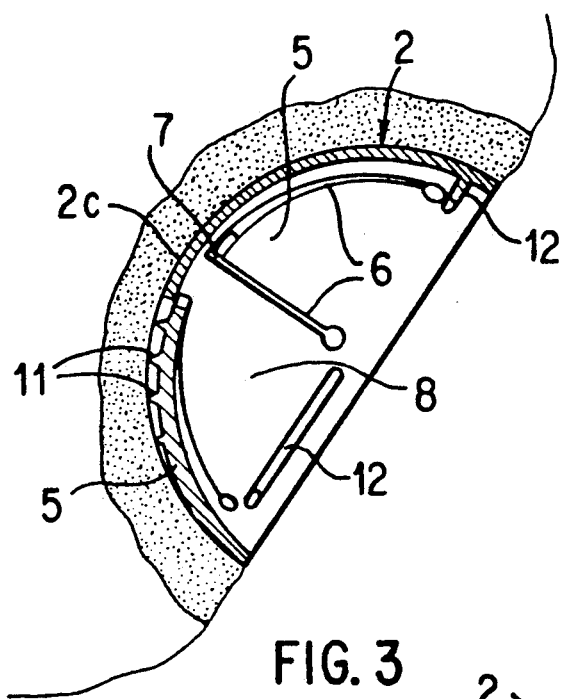
FIG. 3 is a view in cross-section along 3—3 in FIG. 1 showing the outer shell along after it has been introduced into the cotyloid cavity.
Figure 4:
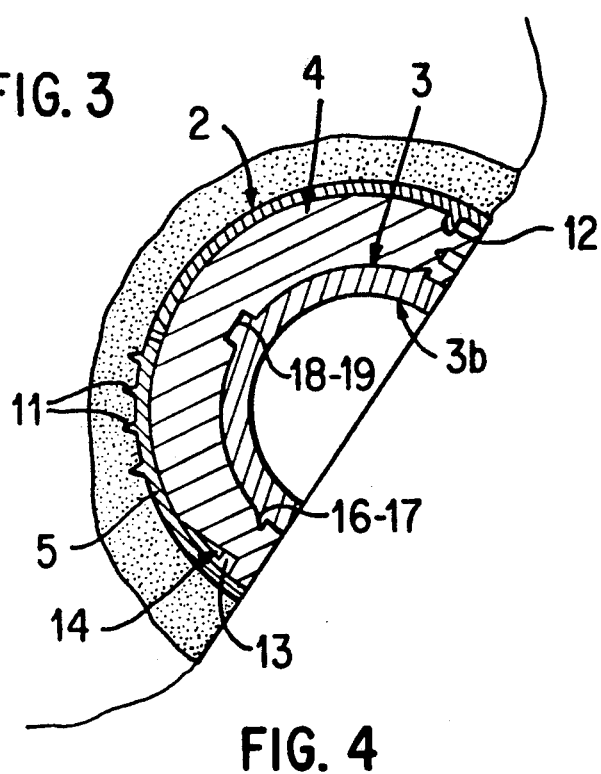
FIG. 4 shows the complete cup after it has been fixed in the cotyloid cavity.

As shown in particular in FIGS. 2 and 4, the cup according to the invention is of the type formed from 3 elements, namely:

an outer spherical shell 2 made from rigid biocompatible material, such as stainless steel or titanium, intended to be secured in the cotyloid cavity of the patient, an inner spherical shell 3 made from hard biocompatible material, such as from alumina or zirconia ceramic or other similar material, at least the inner surface 3b of which has a small coefficient of friction relative to the material forming the cephalic head of the femoral element associated with this cup and which is generally made from an appropriately selected ceramic, an intermediate spherical shell 4 made from a flexible material such as low-density polyethylene and which is intended to perform a cushioning role between the inner shell 3 and the outer shell, in order to prevent the sudden transmission to the latter of the substantial vertical forces which are capable of shaking it to a point where the quality of its fixing deteriorates.

The outer shell 2 has tongues 5, which can move radially, in the form of portions of sectors of a spherical shell and each of which is established by two slits in arcs of a circle 6, with a regular angular distribution and the ends of which are situated near the edge 2a of the opening 2b of this shell and near its vertex 2c, respectively. The ends of the two slits 6, establishing a single tongue 5 and situated near the vertex 2c of the shell 2, are furthermore connected by a partially annular slit 7 situated on the same circle as the slits 7 of the other tonges 5, this circle being concentric with the vertex 2c of the shell 2.

Figure 1:
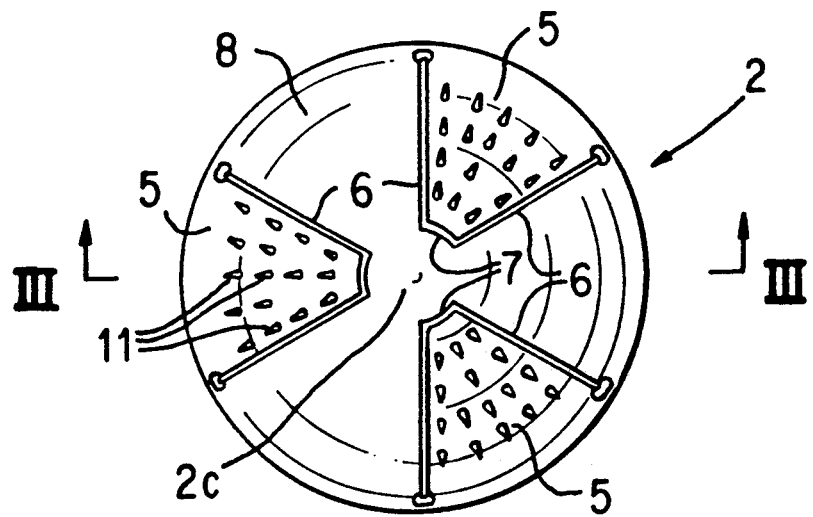
FIG. 1 is a plan view from above.

As shown in particular in FIG. 1, each tongue 5 of the shell 2, which in this example has three, is joined to the shell 2 by its large-sized end situated near the opening 2b of the shell. It may be noted that two adjacent tongues 5 are separated from each other by a portion of a sector of a spherical shell 8 similar to the tongues 5 but immobile, its effect being to preserve a sufficient rigidity for the shell 8 to prevent it from deforming.

Each tongue 5, which is capable of pivoting about its large side or its large base, as indicated by the double arrow 9 in FIG. 2, carries, on its outer surface, securing spikes 11 which are oriented substantially radially, in other words on the radius of rotation of the tongue which has as its axis of pivoting its edge adjacent to the opening 2b of this shell 2. The arrangement of the spikes and their pyramid shape promote their penetration on this radius into the cotyloid cavity.

Figure 5:
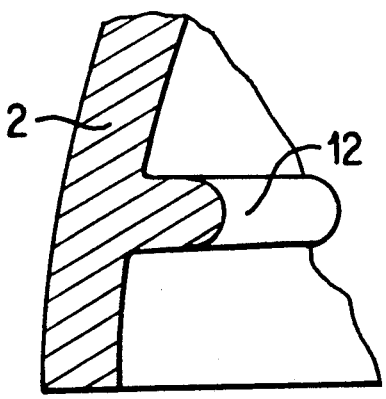
FIG. 5 is, on a larger scale, a partial view in cross-section along 5—5 in FIG. 2.
Figure 6:
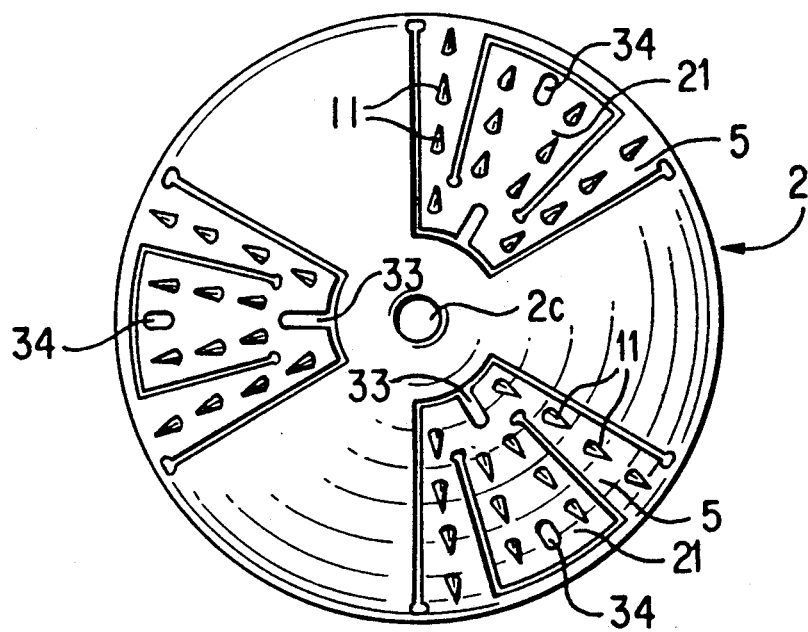
FIG. 6 is a plan view from above similar to FIG. 1 illustrating an alternative embodiment of this cup.

FIGS. 2 and 5 also show an advantageous embodiment of the means for assembling the intermediate shell 4 with the outer shell 2. For this purpose, the shell 2 carries, on its internal surface and near the edge of its opening 2b, three rib segments 12 belonging to the same circle 12a parallel to the plane of the opening 2b and each of which is intended to form one of the male fastening catches of a fastening system of the bayonet type. Each rib segment 12 extends over an arc of a circle less than 60°.

For its part, the intermediate shell 4 has, on its outer surface, three groove segments 13 having the same regular angular distribution as the rib segments 12 but being substantially twice their length. An entry notch 14 is arranged at each of the ends corresponding to each of the throats 13 in order to enable each of them to engage on one of the ribs 12 by an axial inserting movement, in other words in the direction of the arrow 15, followed by a rotating movement about its radius perpendicular to the plane of its opening 4a.

This fastening or assembly system, of the bayonet type, has the advantage of being much quicker to use than any other known system using a cylindrical or conical screwthread which obviously requires several complete rotations to be made in order to achieve assembly.

FIG. 2 also shows the method for assembling the inner shell 3 with the intermediate shell 4 and which is of the snap-fit type. For this purpose, on the one hand, the inner shell 3 has a circular peripheral rib 16, parallel to the plane of its opening 3a, whereas the intermediate shell 4 has, in its spherical cavity 4b, a peripheral circular throat 17, with a cross-section which complements that of the rib 16, the engagement of the rib 16 in the groove 17 being facilitated by the elasticity of the material forming the shell 4. It may be readily appreciated that the inner 3 and intermediate 4 shells may also be assembled instantaneously.

In order to improve the mechanical joint between the inner shell 3 and the intermediate shell 4, it is possible to provide furthermore, as shown in FIG. 2, on the vertex of the outer surface of the inner shell 3, a stud 18 which can engage in a housing 19, arranged to receive it, at the vertex or pole of the cavity 4b of the intermediate element 4.

It was mentioned above that the inner shell 3 has an inner cavity 3b manifesting a very small coefficient of friction with the material forming the cephalic head of the femoral element. For this purpose, this inner cavity 3b is advantageously formed from an alumina or zirconia ceramic or any other appropriate ceramic.

The design of this cup shows quite evidently that, as a result of the structure of its outer shell 2, it has a virtually undeformable opening diameter 2b, which considerably reduces any risk of relative movement of this outer shell 2 relative to the cotyloid cavity in which it is fixed, and thus the risk of a dislocation.

In order to enable this cup to be fitted and withdrawn without damaging the acetabulum, as shown very clearly in FIG. 1, it is preferable not to provide spikes 11 close to the base of each tongue 5, in other words near its end with which it is connected to the outer shell 2. Indeed, because of its joint with the shell 2, this part of each tongue 5 may only undergo a small pivoting movement such that if it were covered with spikes, it would not be possible to retract the latter and they would hinder the positioning of the shell. The result of this is that the securing of the outer shell in the acetabulum is far from excellent near its opening. In order to overcome this, according to an improved embodiment of the invention, a secondary tongue 21, inverted relative to the first, is cut out from each main tongue 5, each secondary tongue 21 being connected to the main tongue 5 which carries it by its end closest to the vertex 2c of the outer shell 2.

Furthermore, the free end of each secondary tongue 21 is situated close to the free edge of this shell 2, surrounding its opening 2b.

Figure 7:
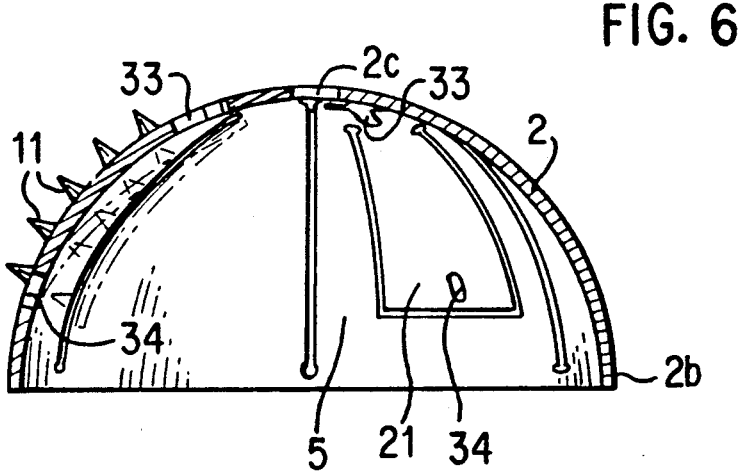
FIG. 7 is a view in cross-section along VII—VII in FIG. 6, showing all the tongues in the retracted position.
Figure 8:
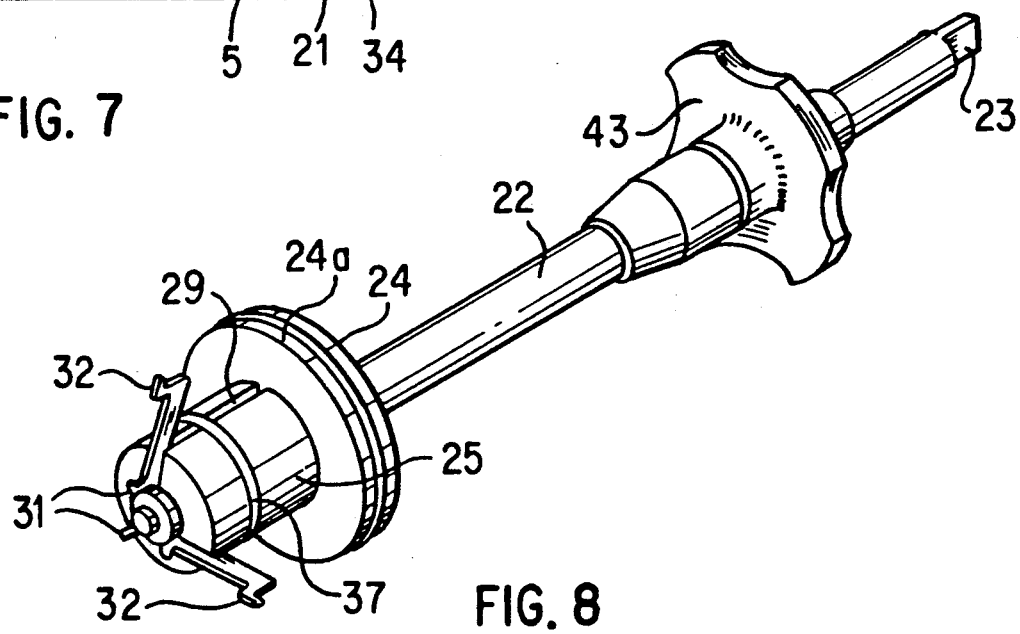
FIG. 8 is a perspective view of a device for positioning or withdrawing the outer shell of this cup.

As is shown in particular in FIG. 7, the presence of these secondary tongues 21 which are capable of being bent towards the inside of the outer shell 2 by pivoting about their base or end closest to the vertex 2c of this shell, enables the spikes 11 which they carry close to their free end, in other words close to the opening 2b of the shell 2 to be retracted and they consequently do not hinder the positioning of the shell 2. Subsequently, after impaction, engagement of the spikes in the acetabulum considerably improves the retention of the outer shell 2, and consequently the cup, in the cotyloid cavity of the patient.

The fitting of this outer shell in the cotyloid cavity therefore requires that the main 5 and secondary 21 tongues be brought beforehand into the retracted position, as illustrated in FIG. 7, so as not to be hindered by the presence of the securing spikes 11 on their outer surface. For this purpose, the device shown in FIGS. 8 to 11, specially designed for this operation, may be used.

As shown in these figures, this device essentially comprises a tubular neck 22, the rear end 22a of which carries a tang 23 enabling it to be adapted to a device of a known type for setting and adjusting the angle of orientation of the outer shell 2 in the acetabulum of the patient.

At its front end 22b, the tubular neck 22 carries a head in the form of a circular plate 24.

On its surface opposite that of the neck 22, the plate 24 has a cylindrical shoulder 24a intended to center the outer shell 2 and having, for this purpose, the same diameter as the inner edge of its opening 2b.

On this same surface, the plate 24 carries a cylindrical piece 25 coaxial with the plate and with the tubular neck 22, which is fixed to it by engaging in a central bore 24b, which it has in order to receive the piece.

This cylindrical piece 25 has, at its end engaged in the bore 24b of the plate 24, an axial cylindrical recess 25a serving for housing, and with the possibility of axially displacing, a collar 26 carried by the tubular neck 22.

The difference between the length of the collar 26 and that of its housing 25a determines its axial movement.

This collar 26 carries three pins 27, only one of which can be seen in FIGS. 9 to 11, and which are arranged orthogonally to the neck 22, with a regular angular distribution about this neck.

A lever 28, normally parallel to the axis 22c of the tubular neck 22 and oriented in the direction opposite that of the tubular neck 22, is articulated on each pin 27.

Each lever 28 is housed in a radial notch 29, provided to receive it, in the cylindrical piece 25.

Each lever 28 has, at its end opposite that by which it is articulated to the corresponding pin 27, two hooks, 31 and 32 respectively, the fastening tip of which is oriented radially outwards relative to the axis 22c of the tubular neck 22. Each hook 31 and 32 is intended to be engaged in a notch 33 and a slot 34 respectively provided to receive it, in each main tongue 5 and in each secondary tongue 21 respectively, and the use of which will be described later.

These notches 33 and slots 34 are centered on the central meridian of the corresponding tongues 5 and 21.

Each notch bottom 29 has a projection 30 directed radially outwards and each lever 28 has, on its surface turned towards the bottom of the notch 29 serving as a housing therefor, an inverted projection 40, these two projections 30 and 40 being arranged such that, when the levers 28 are in the most outwardly advanced position, in other words in the position corresponding to the limit of the movement of the collar 26 against the bottom of its housing 25a furthest from the rear end 22a of the tubular neck 22, as illustrated in FIG. 9, the projection 40 carried by each lever 28 is arranged just in front of the projection 30 carried by the corresponding bottom of the notch 29.

It may be readily appreciated that an axial displacement of the collar 26 towards the opposite bottom of its housing 25a, in other words in the direction of the arrow 35, causes the projections 40 of the levers 28 to mount the projections 30 of the bottoms of their notches 29, and consequently to pivot each lever 28 radially outwards, in other words in the direction of the arrow 36 for the lever 28 which can be seen in FIGS. 9 to 11.

This pivoting, which is caused by only a very small fraction of the axial movement of the collar 26, in the direction of the arrow 35, causes the hooks 31 and 32 to engage on the notch bottom 33 and on the slot bottom 34 respectively such that each hook 28, by continuing its displacement in the direction of the arrow 35, causes the corresponding main 5 and secondary 21 tongues to flex towards the inside of the outer shell 2, as illustrated in FIGS. 10 and 11, until their spikes 11 are completely retracted relative to the outer surface of the shell 2, in other words in the position illustrated in FIG. 11.

As shown in FIGS. 10 and 11, the engagement of the hooks 31 and 32 in the notch 33 and slot 34 bottoms, combined with the bending of the main 5 and secondary 21 tongues, makes any untoward disengagement of the hooks impossible, in spite of the presence of an annular spring 37 surrounding the levers 28 and tending constantly to return them to their original position parallel to the axis 22c of the tubular neck 22.

It is indeed essential that the levers 28 be constantly returned to their position parallel to the axis 22c of the tubular neck 22, so that their hooks 31 and 32 can be engaged in the notches 33 and slots 34, in spite, in particular, of the action of the weight tending to pivot some of them in the direction illustrated by the arrow 36.

In the example shown in FIGS. 8 to 11, the means for actuating the collar 26, in the direction of the arrow 35 and in the reverse direction, consist of a control rod 38 housed in the bore 22d of the tubular neck 22, the front end 38a of which is connected axially by a pin 39 to the collar 26 and the rear end 38b of which is connected axially by a pin 41 to a threaded ring 42 mounted in a tapped bore 43a of an operating wheel 43 carried by the tubular neck 22.

This device is therefore used as follows:

Once the operating wheel 43 has been pivoted by the surgeon in the direction corresponding to the displacement of the threaded ring 42 and of the collar 26, in the direction opposite that of the arrow 35, in other words in the direction of the arrow 44, the levers 28 and their hooks 31 and 32 are brought into their most advanced position.

The surgeon may then engage the outer shell 2 on the levers 28, on the one hand, until each hook 31 and 32 projects beyond the tongues, 5 and 21 respectively, through the notches 33 and the slots 34 and, on the other hand, until the peripheral edge of its opening 2b is centered relative to the plate 24 by its engagement on the shoulder 24a of the latter.

Whilst holding the shell 2 in this position, the surgeon can operate the wheel 43 in the reverse direction in order to displace the threaded ring 42 and the collar 26 in the reverse direction, in other words in the direction of the arrow 35.

As mentioned above, when the levers 28 are displaced in the direction of the arrow 35 and they have subsequently pivoted radially outwards, their hooks 31 and 32 engage on the bottoms of notches 33 and slots 34 of the main 5 and secondary 21 tongues, as indicated above and illustrated in FIGS. 10 and 11. Continuing this displacement of the levers 28 in the direction of the arrow 35 therefore causes the tongues 5 and 21 to flex.

Once the spikes 11 of the main 5 and secondary 21 tongues have then been brought into the retracted position, as illustrated in FIG. 11, the surgeon may then mount the device, via the tang 23 of its rear end 22a on a setting and guide device enabling him to position the shell 2 very correctly in the cotyloid cavity of the patient.

This operation may be performed significantly more easily with all the spikes 11 retracted.

When the shell 2 is in its correct angular position, the surgeon then needs to operate the wheel 43 again in the reverse direction from that indicated previously in order to displace the threaded ring 42, the collar 26 and the levers 28 in the reverse direction, in other words in the direction illustrated by the arrow 44.

The result of this is that, by their displacement in this direction, the levers 28 and their hooks 31 and 32 gradually free the main 5 and secondary 21 tongues which then tend to resume their original position, illustrated in FIG. 9, as a result of the elasticity of the material from which they are formed.

Given that their spikes 11 can encounter resistance in contact with the acetabulum of the patient, the operation of the wheel 43 will be slowed down, all the tongues, 5 and 21, being prevented by this resistance from moving towards their rest position. The surgeon will then have to apply shocks to the device, for example using the fly-weight with which the setting and adjusting unit is generally equipped, which shocks will force the spikes 11 to penetrate the acetabulum.

By successively repeating several times the operation of the wheel 43 in the lastmentioned direction, and that of the fly-weight, the surgeon will be able to obtain the complete fixing of the shell 2 in the acetabulum.

It is worth noting that the direction of pivoting of the main tongues and penetration of their spikes 11 into the acetabulum causes a tensile force, oriented in the direction of the arrow 44, to be exerted on the shell 2, which ensures an excellent application of the shell 2 against the acetabulum.

With operations similar to those mentioned above, it will naturally be possible to withdraw without any difficulty a shell 2 from the acetabulum of a patient if, for example, this shell needs to be replaced, as a result of any deterioration, and in particular as a result of deterioration of the acetabulum of this patient.

The intermediate shell 4 is then engaged and fixed in the outer shell 2, preferably after the shell 3 has been preassembled with it. The positioning of the intermediate shell 4 naturally locks the tongues 5 of the outer shell 2, preventing them from pivoting towards the inside of this shell, which contributes to ensuring that the securing position is maintained.

Given that the outer shape of the outer shell 2, after the cup has been fitted, corresponds to the shape which it occupies, naturally before it has been fitted, it is entirely possible and easy to arrange in the cotyloid cavity of the patient a cradle with a complementary shape against which the outer shell 2 of this cup will be applied with a close contact.

This undeformable nature of the diameter of the opening 2b of the outer shell 2 enables an intermediate shell 4 to be used, without any risk of untoward displacement or dislocation, which has relatively substantial qualities of flexibility and elasticity which give rise to a considerable improvement in the cushioning function of this intermediate shell 4 relative to prior known cups. The flexibility of this intermediate shell 4 also contributes to ensuring a close contact between the three elements of this cup, with the result that an excellent distribution of the stresses transmitted by the femur to the hip of the patient is thus obtained.

I claim:

1. An acetabular cup having a polar region and an opposite equatorial region, said cup being adapted to be cementlessly affixed to a prepared acetabulum, comprising:
   a spherical inner shell formed of a biocompatible hard material having a low coefficient of friction;
   a spherical intermediate shell formed of a biocompatible semi-rigid, elastic material;
   a rigid, spherical outer shell formed of a biocompatible material, said outer shell being divided into movable segments, said movable segments having projection means extending radially outwardly therefrom, said segments being defined by a pair of arcuate slits extending along the longitudinal direction between the polar and equatorial regions and a latitudinal slit intersecting said arcuate slits near the polar region, wherein each segment can be displaced radially outwardly forcing the projection means into the adjacent bone.

2. An acetabular cup as in claim 1, wherein at least one of the movable segments includes a secondary movable segment, said secondary segment being defined by a second pair of arcuate slits, said secondary segment having projection means extending radially outwardly therefrom.

3. An acetabular cup as in claim 2, wherein the secondary segment is further defined by a latitudinal slit intersecting the second pair of arcuate slits near the equatorial region.

4. An acetabular cup as in claim 1, comprising:
   means for mounting the inner shell on the intermediate shell; and
   means for mounting the intermediate shell on the outer shell.

5. An acetabular cup as in claim 4, wherein the means for mounting the intermediate shell on the outer shell comprises a bayonet fastening means.

6. An acetabular cup as in claim 4, wherein the means for mounting the inner shell on the intermediate shell comprises a snap fitting.

7. A acetabular cup as in claim 6, wherein the snap fitting comprises a raised rib formed on the inner shell and a groove for receiving said rib formed on the intermediate shell.

8. An acetabular cup as in claim 7, comprising a stud extending from the inner shell and a cavity for receiving the stud in the intermediate shell, whereby rotation between the inner and intermediate shells is prevented.

9. An acetabular cup as in claim 1, wherein the inner shell is of a ceramic material.

10. An acetabular cup as in claim 9, wherein the ceramic material is selected from the group consisting of alumina ceramic and zirconia ceramic.

11. An acetabular cup as in claim 1, wherein the intermediate shell is of low density polyethylene.

12. An acetabular cup as in claim 1, wherein the outer shell is of a material selected from the group consisting of stainless steel and titanium.

* * * * *